United States Patent
Chen

(10) Patent No.: US 9,449,780 B2
(45) Date of Patent: Sep. 20, 2016

(54) X-RAY ANALYZER HAVING MULTIPLE EXCITATION ENERGY BANDS PRODUCED USING MULTI-MATERIAL X-RAY TUBE ANODES AND MONOCHROMATING OPTICS

(71) Applicant: X-RAY OPTICAL SYSTEMS, INC., East Greenbush, NY (US)

(72) Inventor: Zewu Chen, Schenectady, NY (US)

(73) Assignee: X-RAY OPTICAL SYSTEMS, INC., East Greenbush, NY (US)

( * ) Notice: Subject to any disclaimer, the term of this patent is extended or adjusted under 35 U.S.C. 154(b) by 109 days.

(21) Appl. No.: 14/381,023

(22) PCT Filed: Feb. 27, 2013

(86) PCT No.: PCT/US2013/027910
§ 371 (c)(1),
(2) Date: Aug. 26, 2014

(87) PCT Pub. No.: WO2013/130525
PCT Pub. Date: Sep. 6, 2013

(65) Prior Publication Data
US 2015/0043713 A1   Feb. 12, 2015

Related U.S. Application Data

(60) Provisional application No. 61/604,251, filed on Feb. 28, 2012.

(51) Int. Cl.
*G21K 1/06* (2006.01)
*H01J 35/08* (2006.01)
(Continued)

(52) U.S. Cl.
CPC .............. *H01J 35/08* (2013.01); *G01N 23/223* (2013.01); *G21K 1/062* (2013.01); *G21K 1/067* (2013.01);
(Continued)

(58) Field of Classification Search
CPC ........ H01J 35/08; H01J 35/14; G21K 1/062; G21K 1/067; G01N 23/223
USPC ...... 378/45, 121, 82–85, 143, 144, 145, 205
See application file for complete search history.

(56) References Cited

U.S. PATENT DOCUMENTS 4,622,688 A * 11/1986 Diemer .................. H01J 35/08
378/124
5,175,755 A * 12/1992 Kumakhov ............ B82Y 10/00
378/34

(Continued)

FOREIGN PATENT DOCUMENTS

CN         200944095 Y      9/2007
CN         101981651 A      2/2011

(Continued)

OTHER PUBLICATIONS

International Search Report for PCT/US2013/027910 dated Jun. 26, 2013.

*Primary Examiner* — Courtney Thomas
(74) *Attorney, Agent, or Firm* — Jeffrey Klembczyk, Esq.; Kevin P. Radigan, Esq.; Heslin Rothenberg Farley & Mesiti P.C.

(57) ABSTRACT

An x-ray tube includes a target on which electrons impinge to form a diverging x-ray beam. The target has a surface formed from first and second target materials, each tailored to emit a respective x-ray energy profile. A first x-ray optic may be provided for directing the beam toward the sample spot, the first x-ray optic monochromating the diverging x-ray beam to a first energy from the energy emitted by the first target material; and a second x-ray optic may be provided, for directing the beam toward the sample spot, the second x-ray optic monochromating the diverging x-ray beam to a second energy from the energy emitted by the second target material. Fluorescence from the sample spot induced by the first and second monochromated energies is used to measure the concentration of at least one element in the sample, or separately measure elements in a coating and underlying substrate.

16 Claims, 14 Drawing Sheets

(51) Int. Cl.
*G01N 23/223* (2006.01)
*H01J 35/14* (2006.01)

(52) U.S. Cl.
CPC ......... *H01J 35/14* (2013.01); *G21K 2201/062* (2013.01); *H01J 2235/081* (2013.01); *H01J 2235/084* (2013.01); *H01J 2235/088* (2013.01)

(56) References Cited

U.S. PATENT DOCUMENTS

| | | | | |
|---|---|---|---|---|
| 5,192,869 | A * | 3/1993 | Kumakhov | B82Y 10/00 250/505.1 |
| 5,497,008 | A * | 3/1996 | Kumakhov | B82Y 10/00 250/505.1 |
| 5,745,547 | A * | 4/1998 | Xiao | G21K 1/06 250/505.1 |
| 6,285,506 | B1 * | 9/2001 | Chen | G21K 1/06 359/642 |
| 6,317,483 | B1 * | 11/2001 | Chen | B82Y 10/00 378/145 |
| 6,333,965 | B1 | 12/2001 | Van Berkel | |
| 6,934,359 | B2 * | 8/2005 | Chen | B82Y 10/00 378/45 |
| 7,035,374 | B2 * | 4/2006 | Chen | G21K 1/06 378/84 |
| 7,110,506 | B2 * | 9/2006 | Radley | G01N 23/12 378/141 |
| 7,209,545 | B2 * | 4/2007 | Radley | G01N 23/12 378/137 |
| 7,257,193 | B2 * | 8/2007 | Radley | H05G 1/025 378/108 |
| 7,738,630 | B2 * | 6/2010 | Burdett, Jr. | B82Y 10/00 378/84 |

FOREIGN PATENT DOCUMENTS

| | | |
|---|---|---|
| EP | 0127230 A1 | 12/1984 |
| JP | 2000019298 A | 1/2000 |
| JP | 200082430 A | 3/2000 |
| JP | 2000082430 A | 3/2000 |
| JP | 2005228696 A | 8/2005 |
| WO | WO2009111454 A1 | 9/2009 |
| WO | WO2011097115 A1 | 8/2011 |

* cited by examiner

X-RAY ANALYZER HAVING MULTIPLE EXCITATION ENERGY BANDS PRODUCED USING MULTI-MATERIAL X-RAY TUBE ANODES AND MONOCHROMATING OPTICS

CROSS-REFERENCE TO RELATED APPLICATION

This application is a national stage filing under section 371 of International Application No. PCT/US2013/027910, filed on Feb. 27, 2013, and published on Sep. 6, 2013 as WO 2013/130525 A1. In addition, this application claims the benefit of U.S. provisional patent application Ser. No. 61/604,251, filed Feb. 28, 2012, both of which are hereby incorporated herein by reference in their entirety.

U.S. GOVERNMENT INTEREST

Certain parts of this invention have been developed with the assistance of the National Science Foundation, Grant No. IIP-0839615. The U.S. Government may have certain rights in this invention.

BACKGROUND OF THE INVENTION

Current events, e.g., the discovery of toxins in toys, environmental air and water concerns, and resulting regulations dictate an urgent need for an analyzer for toxic element determination. Advanced x-ray fluorescence (XRF) analyzers can play a valuable role in the quantification of such toxins and many other substances of interest in a variety of samples, e.g., toxins in consumer products, and various harmful elements in petroleum products.

As one prominent example, manufacturers, suppliers, distributors, retailers, and regulatory entities need a long-term solution for toxic-element analysis for a wide variety of consumer goods. Many new regulations require manufacturers to detect many elements such as lead (Pb), mercury (Hg), arsenic (As), cadmium (Cd), chromium (Cr), bromine (Br), selenium (Se), antimony (Sb), barium (Ba), and chlorine (Cl). In the EU regulations, the maximum concentration in a homogenous material is 1,000 ppm for hexavalent chromium ($Cr^{6+}$), Hg, Pb, polybrominated biphenyl (PBB), and polybrominated diphenyl ethers (PBDE), and 100 ppm for Cd. The new U.S. regulation (CPSIA) for children's products is much more restrictive. For example, the maximum allowable lead level in toys and children's jewelry is less than or equal to 100 ppm in any accessible part of a product.

Current measurement methods are either accurate enough but not usable on the factory floor, or they may be convenient for use on the factory floor but not close to being sufficiently sensitive or repeatable. As a result, there is a need for a truly fit-for-purpose analyzer for this application. There is a strong market need for a rapid, reliable, convenient, nondestructive, high-sensitivity, quantitative, cost-effective analyzer to carry out critical and conclusive measurements with a single instrument in a manufacturing facility either at-line or on-line, or any place in a distribution chain. Contaminated products can be eliminated at the most advantageous place in the process, substantially mitigating or even eliminating accidental production waste and errors. There is also a strong need for a similar capability at several stages in the distribution and by regulators to verify the compliance of materials and products.

Existing low-cost methods of toxin detection are generally ineffective, e.g., swab tests. Higher-cost methods that provide the requisite accuracy are expensive and time consuming. These methods may involve manually scraping samples, digesting them in acids at elevated temperature and pressure, introducing them into a combustion chamber, and analyzing the combustion product. One widely used method is inductively coupled plasma optical emission spectroscopy (ICP-OES)—a method which is expensive, destructive, and slow. Alternatively, conventional handheld x-ray fluorescence (XRF) guns are rapid and nondestructive, but are only reliable for higher than regulated concentrations, and are averaged across large sample areas, and cannot separately evaluate paint layers.

As discussed further below, the present invention provides a measurement solution with fast, accurate results for toxins in manufactured products, enabled by sophisticated x-ray sample excitation and monochromating optic techniques. Such proprietary optics typically provide 10-1,000× improvements in the ability to focus x-rays; and optic-enabled analyzers are especially suited for these targeted markets—moving measurements from the lab into the factory, field, and clinic.

In x-ray analysis systems, high x-ray beam intensity and small beam spot sizes are important to reduce sample exposure times, increase spatial resolution, and consequently, improve the signal-to-background ratio and overall quality of x-ray analysis measurements. In the past, expensive and powerful x-ray sources in the laboratory, such as rotating anode x-ray tubes or synchrotrons, were the only options available to produce high-intensity x-ray beams. Recently, the development of x-ray optic devices enables collection of the diverging radiation from an x-ray source by focusing the x-rays. A combination of x-ray focusing optics and small, low-power x-ray sources can produce x-ray beams with intensities comparable to those achieved with larger, high-power, and more expensive devices. As a result, systems based on a combination of small, inexpensive x-ray sources, excitation optics, and collection optics are greatly expanding the availability and capabilities of x-ray analysis equipment in, for example, small laboratories and in the field, factory, or clinic, etc.

Monochromatization of x-ray beams in the excitation and/or detection paths is also useful to excite and/or detect very precise portions of the x-ray energy spectrum corresponding to various elements of interest (lead, etc.). X-ray monochromatization technology is based on diffraction of x-rays on optical crystals, for example, germanium (Ge) or silicon (Si) crystals. Curved crystals can provide deflection of diverging radiation from an x-ray source onto a target, as well as providing monochromatization of photons reaching the target. Two common types of curved crystals are known as singly-curved crystals and doubly-curved crystals (DCCs). Using what is known in the art as Rowland circle geometry, singly-curved crystals provide focusing in two dimensions, leaving x-ray radiation unfocused in the third or orthogonal plane. Doubly-curved crystals provide focusing of x-rays from the source to a point target in all three dimensions. This three-dimensional focusing is referred to in the art as "point-to-point" focusing.

Commonly-assigned U.S. Pat. Nos. 6,285,506 and 7,035,374, incorporated by reference herein in their entirety, disclose various configurations of curved x-ray optics for x-ray focusing and monochromatization. In general, these patents disclose a flexible layer of crystalline material (e.g., Si) formed into curved optic elements. The monochromating function and the transmission efficiency of the optic are determined by the crystal structure of the optic.

The ability to focus x-ray radiation to smaller spots with higher intensities, using focusing and monochromating x-ray optics, has enabled reductions in the size and cost of x-ray tubes, and x-ray systems have therefore been proliferating beyond the laboratory to in-situ, field uses. Commonly-assigned U.S. Pat. Nos. 6,934,359 and 7,072,439, incorporated by reference herein in their entirety, disclose monochromatic wavelength dispersive x-ray fluorescence (MWD XRF) techniques and systems, using doubly curved crystal optics in the excitation and/or detection paths. The x-ray optic-enabled systems described in these patents have enjoyed widespread success beyond the laboratory, for example, measuring sulfur in petroleum fuels in a variety of refinery, terminal, and pipeline environments.

In such systems, precise optic alignment along an axis defined by a source and sample spot may be required, as illustrated in above-incorporated U.S. Pat. No. 7,035,374, which proposes an arrangement of curved, monochromating optics around a central axis operating according to Bragg diffraction conditions. FIG. 1a is a representative isometric view of this x-ray optic arrangement 150 having a curved optic 152, an x-ray source location 154, and an x-ray target location 156. X-ray source location 154 and x-ray target location 156 define a source-to-target transmission axis 162. Optic 152 may include a plurality of individual optic crystals 164, all of which may be curved and arranged symmetrically about axis 162. The plurality of crystals 164 may be arranged from a small fraction of a rotation to a full rotation around the source-to-target transmission axis 162.

FIG. 1b is a cross-sectional view taken along section lines 1b-1b of FIG. 1a, wherein the surface of optic 152, x-ray source location 154, and x-ray target location 156 define one or more Rowland (or focal) circles 160 and 161 of radius R for optic 152. Those skilled in the art will recognize that the number and orientation of the Rowland circles associated with crystal optic 152, or individual crystals 164, will vary with the position of the surface of optic crystal 152, for example, the variation of the toroidal position on optic crystal 152.

The internal atomic diffraction planes of optic crystal 152 also may not be parallel to its surface. For example, as shown in FIG. 1b, the atomic diffraction planes of crystal 152 make an angle $\gamma_t$ with the surface upon which x-rays are directed, at the point of tangency 158 of the surface and its corresponding optic circle 160 or 161. $\theta_B$ is the Bragg angle for crystal optic 152 which determines its diffractive effect. Each individual optic crystal can in one example be fabricated according to the method disclosed in above-incorporated U.S. Pat. No. 6,285,506, entitled "Curved Optical Device and Method of Fabrication."

All individual crystals 164 should be aligned to the source-to-target axis 162, for proper Bragg conditions. Improvement in optic alignment, especially for such multiple-crystal optics, therefore remains an important area of interest. Various optic/source combinations have already been proposed to handle thermal stability, beam stability, and alignment issues, such as those disclosed in commonly assigned U.S. Pat. Nos. 7,110,506; 7,209,545; and 7,257,193. Each of these patents is also incorporated herein by reference in its entirety.

The above-described XRF technology and systems have been useful in single-element analyzers for measuring generally homogeneous sample structure (e.g., sulfur in petroleum products). However, the measurement of toxins in manufactured products presents additional levels of challenges. First, an instrument should have the capability to measure more than one element simultaneously or near-simultaneously, from a relatively confined list, for example, the 10 toxic elements, discussed above. Moreover, manufactured products are likely to be heterogeneous in nature, requiring small spot resolution, as well as the ability to detect toxins in one of a number of heterogeneous layers (e.g., the level of lead in a paint layer and separately in a substrate layer beneath the paint).

Improved x-ray analysis method and systems are required, therefore, to address the problems associated with measuring multiple toxins in potentially heterogeneous samples, to enable in-the-factory and/or in-the-field measurement of toxins.

SUMMARY OF THE INVENTION

Disclosed herein are improved, multiple monochromatic x-ray excitation techniques and systems for addressing these problems. These techniques can quantify the levels of toxins (e.g., lead, cadmium, etc) in consumer products at the low levels currently mandated by regulations, and can also differentiate between toxins in paint layers and substrates underlying the paint layers, and also provide other industries (e.g., petroleum) with important elemental analysis capability.

In that regard, the present invention in one aspect is an x-ray analysis apparatus for analyzing a sample spot. An x-ray tube includes a target on which electrons impinge to form a diverging x-ray beam. The target has a surface formed from first and second target materials, each target material tailored to emit a respective energy profile upon impingement by the electrons. A first x-ray optic may be provided for receiving the diverging x-ray beam and directing the beam toward the sample spot, the first x-ray optic monochromating the diverging x-ray beam to a first energy from the energy emitted by the first target material; and a second x-ray optic may also be provided, for receiving the diverging x-ray beam and directing the beam toward the sample spot, the second x-ray optic monochromating the diverging x-ray beam to a second energy from the energy emitted by the second target material. Fluorescence from the sample spot induced by the first and second monochromated energies is used to measure the concentration of at least one element in the sample, or separately measure elements in a coating and underlying substrate.

Three or more target materials may be used for the target. The target materials may be formed in separate layers on the target, or alloyed into a single layer, or a combination of both. The materials may emit characteristic energies and/or bremsstrallung; and the x-ray optics can be tailored to monochromate to particular x-ray energies. Sequencing between tube energies and/or optics can also be provided depending on the measurements needed.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in combination with the accompanying drawings in which:

DETAILED DESCRIPTION OF THE INVENTION

Figure 1A:
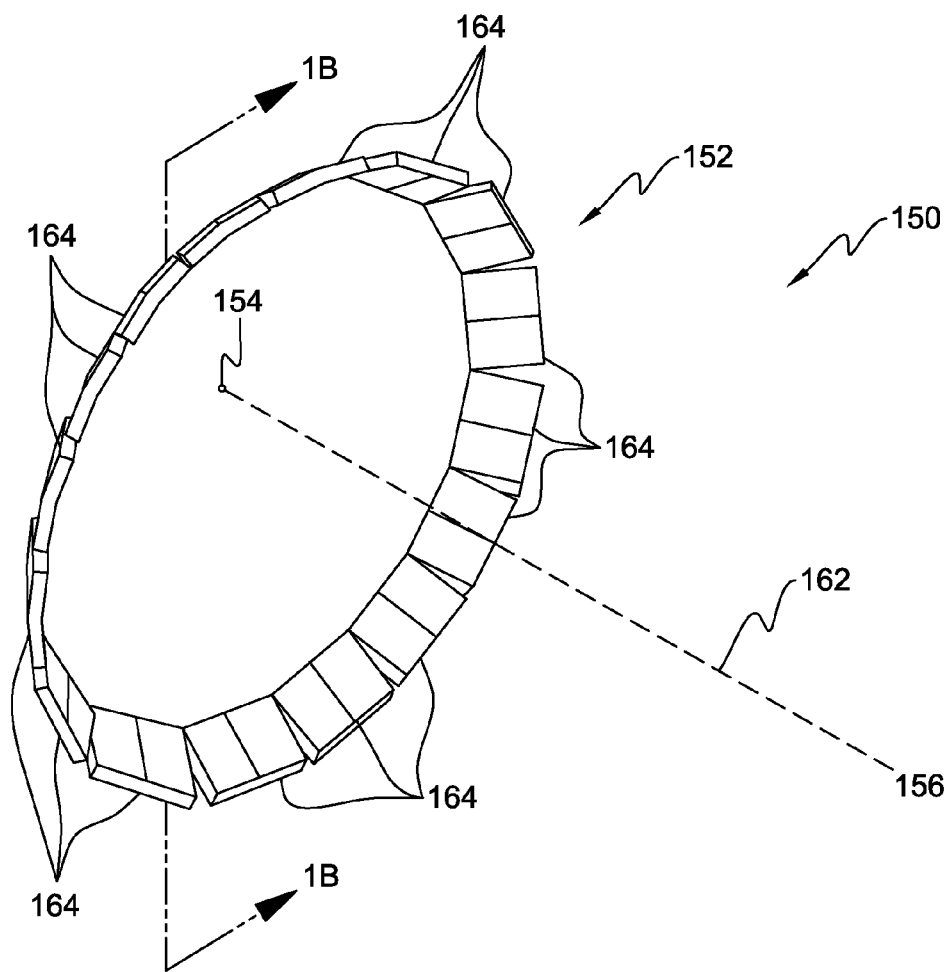
FIGS. 1a-b depict an exemplary arrangement of crystal x-ray optics about an axis, requiring alignment.
Figure 1B:
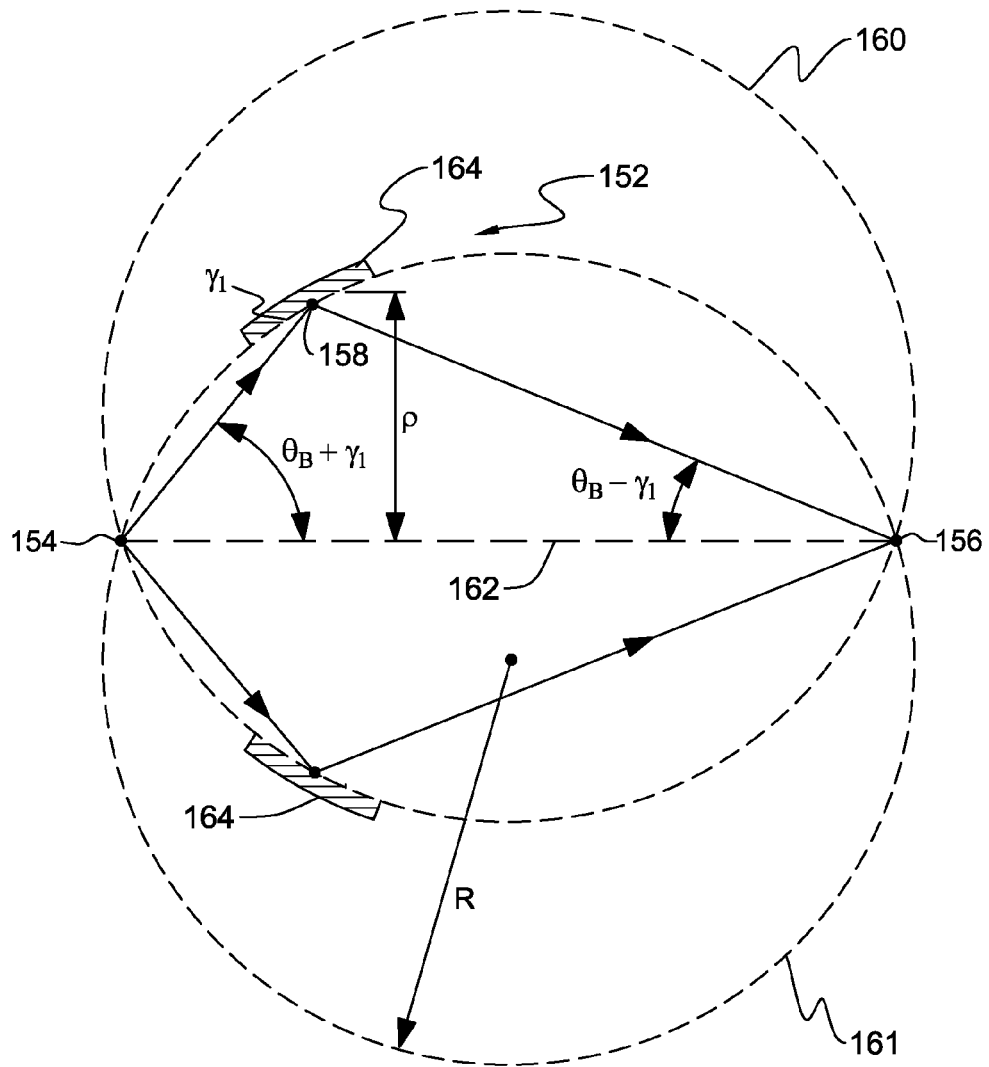
Figure 2:
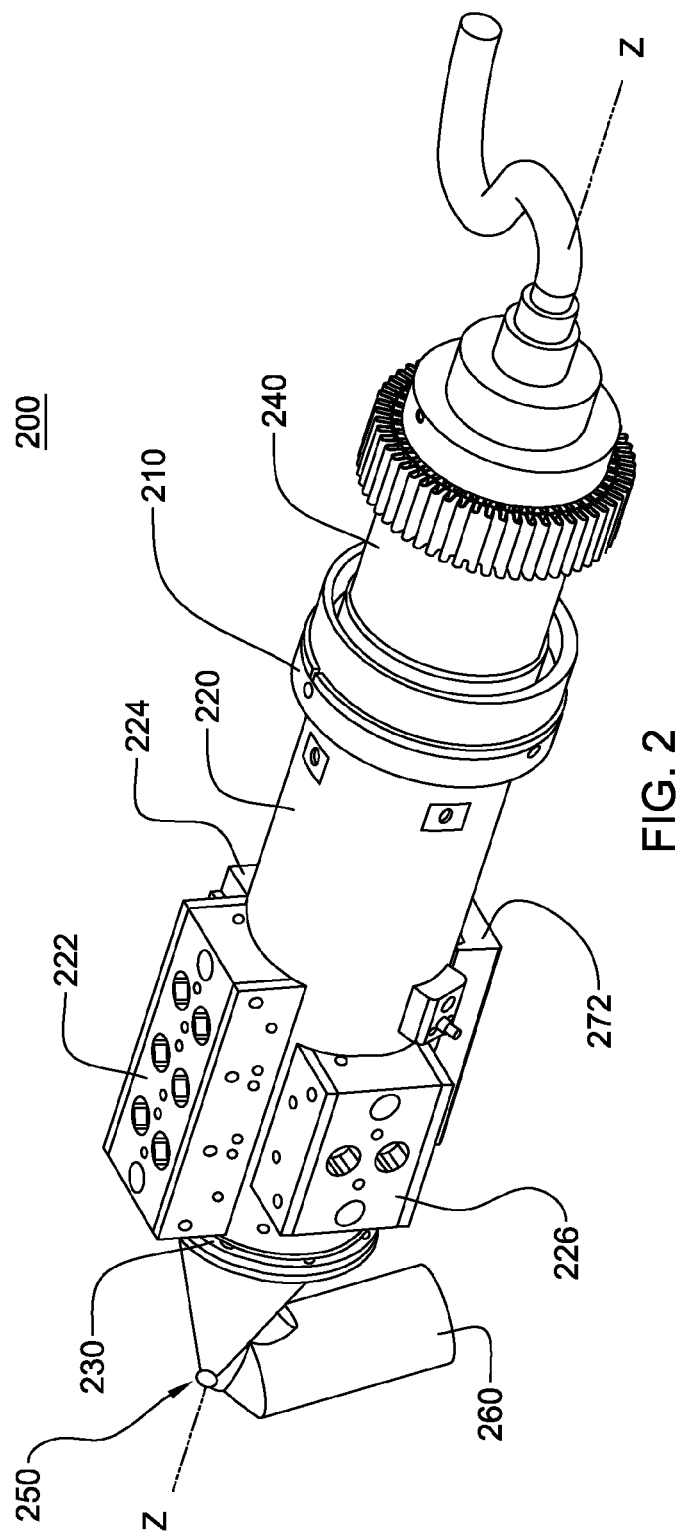
FIG. 2 is a perspective view of an aligned x-ray optic and source assembly, in accordance with one aspect of the present invention.

Improved X-Ray Source Assemblies:

In accordance with the present invention, FIG. 2 depicts one embodiment of a highly-aligned x-ray optic and source assembly 200 in accordance with the present invention. Various aspects of this package have been disclosed in the commonly assigned, previously-filed U.S. Provisional Applications entitled X-RAY OPTIC AND SOURCE ASSEMBLY FOR PRECISION X-RAY ANALYSIS APPLICATIONS, filed Mar. 5, 2008 as Ser. No. 61/033,899; and HIGHLY ALIGNED X-RAY OPTIC AND SOURCE ASSEMBLY FOR PRECISION X-RAY ANALYSIS APPLICATIONS, filed Mar. 25, 2008 as Ser. No. 61/039,220 now U.S. Pat. No. 7,738,630 B2; and XRF SYSTEM HAVING MULTIPLE EXCITATION ENERGY BANDS IN HIGHLY ALIGNED PACKAGE, filed Apr. 7, 2008, as Ser. No. 61/042,974 now U.S. Patent Publication No. 2011/0170666 A1, published Jul. 14, 2011; previously filed PCT Application entitled XRF SYSTEM HAVING MULTIPLE EXCITATION ENERGY BANDS IN HIGHLY ALIGNED PACKAGE, filed Mar. 3, 2009 as serial no. PCT/US2009/035847; and SUPPORT STRUCTURE FOR MULTIPLE HIGHLY ALIGNED X-RAY OPTICS filed Oct. 26, 2011 as Ser. No. 61/551,602; each of which is assigned to X-Ray Optical Systems, Inc., the assignee of the present invention, and each of which is hereby incorporated herein by reference in its entirety.

As discussed in those Applications, the assembly may include a first section 210, second section 220, and third section 230, which together align an x-ray tube 240 to a sample spot 250, along a central transmission axis Z. Also aligned along this axis are multiple optic carriage assemblies 222, 224, and 226 which hold exemplary monochromating optics also requiring alignment to transmission axis Z (as discussed elsewhere herein).

The ability to provide an efficient, economical, portable analysis capability depends to a large extent upon x-ray tube and optic technology. In that regard, certain tube and optic technology can be combined for smaller, portable systems, e.g., a compact, electron-bombardment x-ray tube. One example of this type of x-ray tube is available from Oxford Instruments—series #5000, which operates at less than 100 watts (i.e., 75 watts) at a cost of less than $2000 per tube, in contrast to higher-power, laboratory sources which can cost many thousands, or hundreds of thousands of dollars—which is cost prohibitive for many applications. Another example is the Varian VF-50J (similar to that depicted here), tubular in shape, and which operates at 50 watts or less, at a cost of several thousand dollars each, with a molybdenum (or other) material, as discussed further below.

Sections 210, 220, and 230 are shown in a form of an exemplary tubular shape. Specifically, the sections are shown in the approximate form of a cylinder, with a circular cross-section, which is one type of tubular shape. The cross-section of tubular sections 210 and 220 could also be square, rectangular, etc. The tubular shapes shown, with circular cross-sections, provide a section-section alignment technique using outer perimeter mating surfaces and inner perimeter mating surfaces.

Second section 220 also accommodates the attachment of optic carriages 222, 224, and 226, which may be fabricated to adjustably mount and align x-ray optics (not shown) respectively, to section 220 and, ultimately, to transmission axis Z; or (not shown) this section can be formed according to the above-incorporated U.S. patent application entitled SUPPORT STRUCTURE FOR MULTIPLE HIGHLY ALIGNED X-RAY OPTICS. X-ray beam focusing and/or monochromating can be accomplished using certain focusing and/or collimating optics, for example, curved crystal monochromating optics such as those disclosed in commonly assigned U.S. Pat. Nos. 6,285,506; 6,317,483; and 7,035,374; and/or multilayer optics; and/or HOPG optics; and/or polycapillary optics such as those disclosed in commonly assigned U.S. Pat. Nos. 5,192,869; 5,175,755; 5,497,008; 5,745,547; 5,570,408; and 5,604,353. Each of the above-noted patents is incorporated herein by reference in its entirety. Of particular interest are curved monochromating optics (discussed elsewhere herein), which require precise alignment along, and a certain distance from, the transmission axis to meet the appropriate Bragg conditions of interest.

Third housing section 230 may include an aperture at the tip of its nose cone, which requires alignment to transmission axis Z for proper illumination of sample spot 250 with the focused x-ray beam(s) from the optic(s). A cone within this section may also be included for additional shielding, rigidly or adjustably mounted to section 230. Section 230 may also have rigidly mounted thereon an exemplary energy-dispersive detector 260 which itself requires close alignment to transmission axis Z. Section 230 and/or its nose cone can also be adjusted in directions orthogonal to the transmission axis Z. Other types of optics and detectors (e.g., wavelength dispersive) may also be used with or without similar optics in the detection path.

Also shown is an automated shutter system having its own carriage 272, which can be used for x-ray safety purposes (i.e., full blocking shutter), and also for selecting which x-ray beams (from the optics) should be applied to the sample, in any mix ranging from individual non-simultaneous excitation, to full simultaneous excitation, or any mix thereof. This is especially important for the multiple-energy excitation techniques discussed below.

In accordance with another aspect of the present invention, multiple optics of apparatus 200 may be different, i.e., may be tuned to different parts of the x-ray energy spectrum, to optimize element detection and quantification in respective areas of the x-ray energy band. In general, for an element to fluoresce and therefore be subject to detection and measurement, the excitation energy must be at or above the element's x-ray absorption edge. Causing all of the elements of interest to fluoresce therefore requires excitation energy above the absorption edges of the elements of interest.

Figure 3:
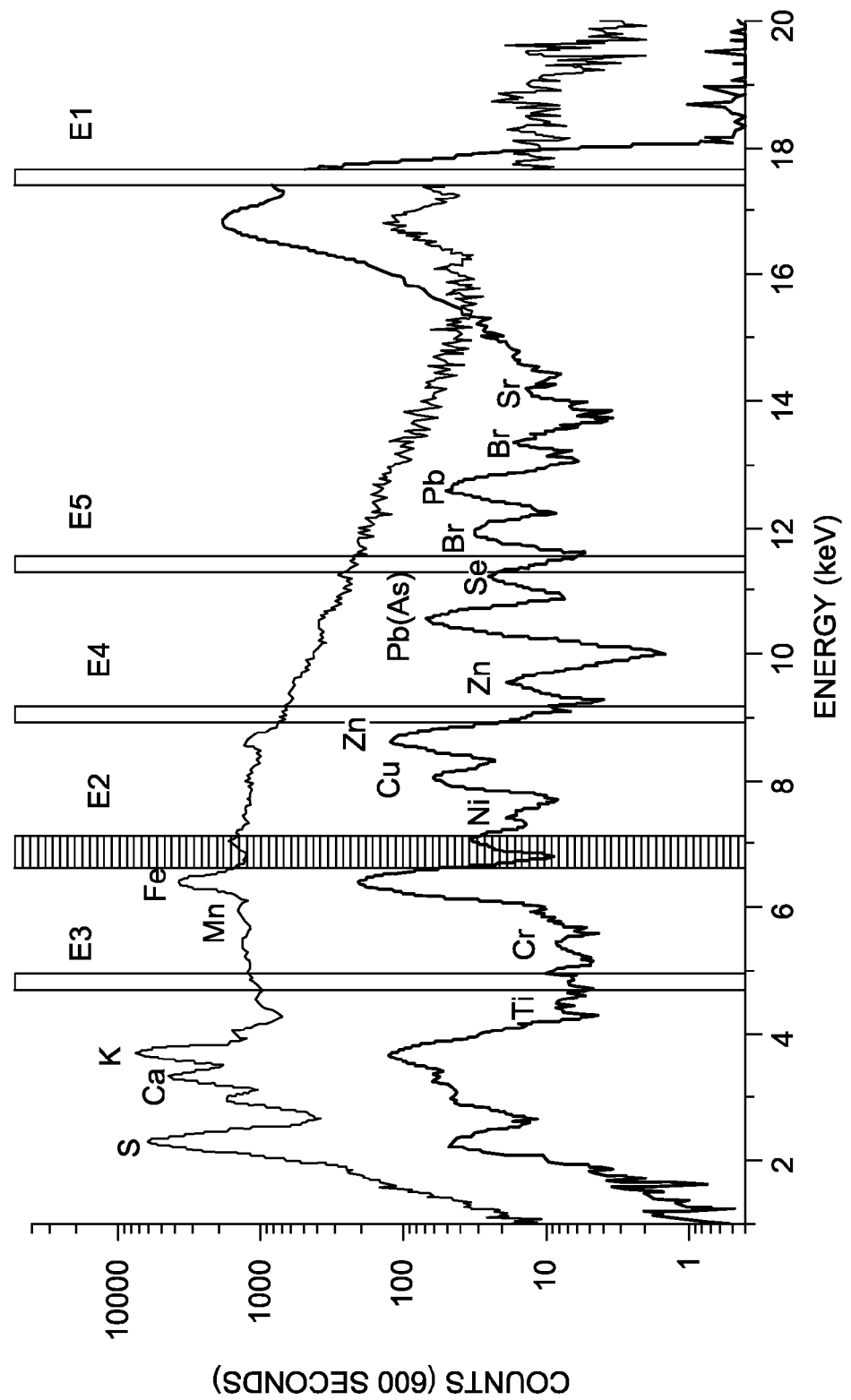
FIG. 3 show the various element peaks due to monochromated excitation energy, and the potential placement of multiple, monochromatic excitation energy beams, in accordance with the present invention.

As an example, and with reference to FIG. 3, a characteristic energy line E1 from, e.g., a molybdenum target x-ray tube at approximately 17 keV, can be focused to the sample using a point-focusing, monochromating optic as discussed above, generally causing all elements having fluorescent lines of interest lower that 17 keV to fluoresce. Its excitation effect gradually diminishes, however, for elements having fluorescence lines much lower (e.g., less than 10 keV in this example).

In accordance with the present invention, additional optic(s) can be employed to simultaneously capture the non-characteristic, broad bremsstrallung energy transmitted from the same x-ray tube, and provide additional lines of excitation energy, at e.g., energies E2, E3, E4, E5 . . . each line from a respective point-focusing, monochromating optic. As discussed further below, energies higher than 17 keV (not shown) can also be used. This technique can be used for efficient, low-background excitation of various ranges of elements in the periodic table. These optics can also be employed to capture different characteristic energies from the tube, when the tube includes multiple materials having respective characteristic lines.

In the one exemplary system embodiment 200 discussed above, three optics provide the 31 keV (from bremsstrallung), the 17 keV characteristic molybdenum line, along with the 7 keV line (also from bremsstrahlung), respectively.

These lines may provide optimized excitation of the following approximate ranges of elements of interest from the periodic table (listed along with their atomic numbers):

31 keV: From about Zr (40) to Te (52)

17 keV: From about Cl (17) to Br (35); Rb(37) to Sr(38); Zr(40);

Cs(55) to Bi(83); Th(90); U(92)

7 keV: From about Al (13) to Co (27)

By using different optics and tube materials, different excitation angles and/or energies can be simultaneously (or sequentially, or any mix thereof using a shutter system) applied to the sample. Because different energies cause different fluorescence effects, more information can be determined in the detection path. For example, higher energies penetrate deeper depths and can be used to detect substrate (rather than painted) layers in the material. Moreover, even though lower energies may penetrate the paint levels, the resultant fluorescence may not, giving more insight into material makeup.

Certain elements may exist in the energy band at spacings that generally exceed a detector's ability to resolve (e.g., Cd and Sn), and in fact have overlapping K/L lines and absorption energies. And tin (Sn), a commonly used lead substitute, may mask the cadmium in the detection path. Therefore, excitation just below the absorption of the higher element (Sn), thereby not exciting the tin but effectively exciting all the cadmium, can be used to isolate the lower element (Cd).

Ratios of fluorescence spectra caused by two different excitation energies can also be exploited for additional information about the sample.

Figure 4A:
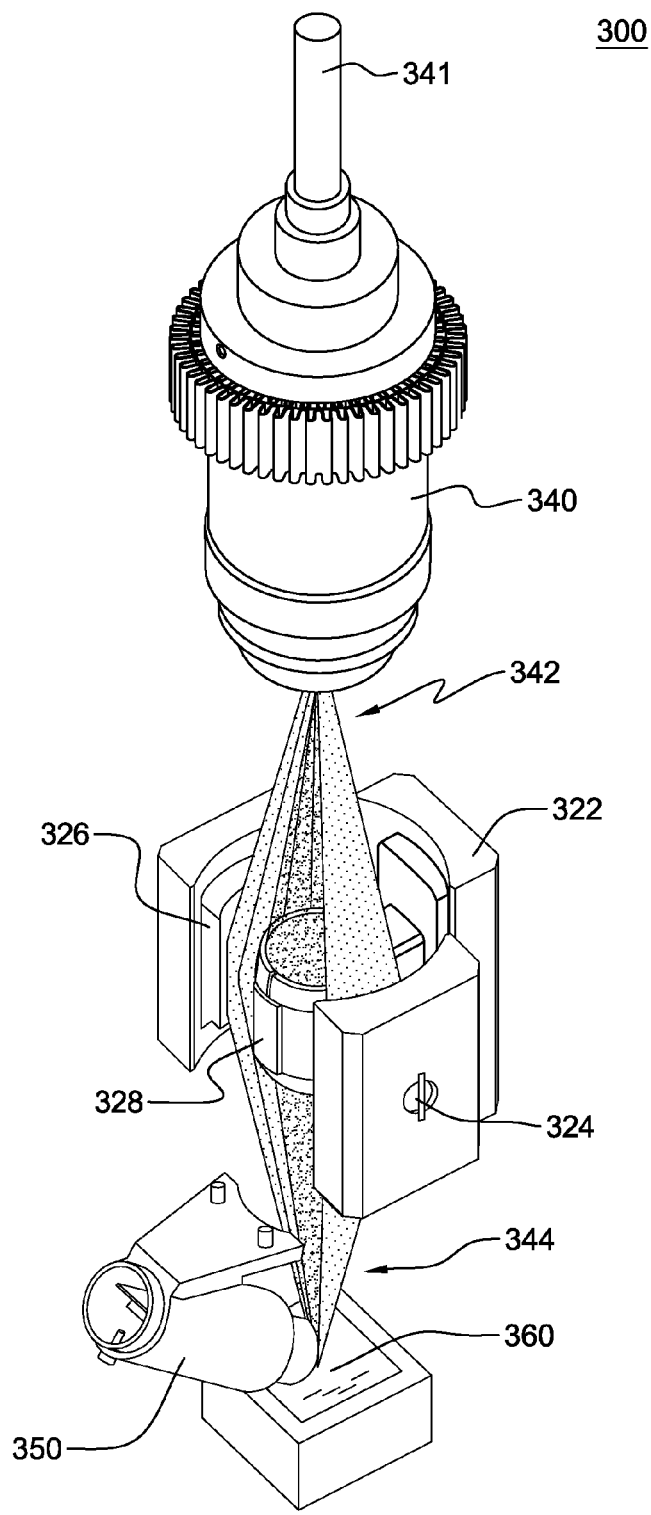
FIGS. 4a-b are schematic views of EDXRF and MWDXRF analyzer designs with improved excitation x-ray tubes in accordance with the present invention.

Improved X-Ray Engines:

An improved EDXRF engine 300 in accordance with the present invention is shown in schematic form in FIG. 4a, in the exemplary form of a small spot tri-chromatic system with a low (326), medium (324), and high (328) energy excitation beams. The unit consists of these three DCC optics, one small-spot x-ray tube 340 producing a diverging x-ray beam 342, and an energy-dispersive detector 350. Three DCC optics with a short focal distance may be used to focus low, medium, and high-energy x-rays 344 to a single spot on a sample 360 to stimulate fluorescence. A short focal distance can enable a very compact geometry. Unlike low and medium-energy optics, the high-energy optic may diffract Bremsstrahlung or other characteristic line photons which are emitted with low intensity from the source, or from different materials on the tube. As discussed further below, an innovative, 360° multi-layer DCC optic may be used to obtain high x-ray flux for example, for low level Cd and Sb analysis. An energy dispersive detector 350, in one embodiment a silicon drift detector (SDD), is used to analyze the fluorescence spectrum. The whole system can be designed to be about 45×40×30 cm (18×16×12 in) and weigh about 9 kg (20 lb), thereby meeting the operational requirements (e.g., at-line or on-line) discussed above.

In this analyzer, the scattered peaks of the three beams can be measured because of the low spectral background provided by monochromatic excitation. More importantly, the scattered peaks from all three energies provide very useful information for quantitative analysis of a layered sample. The difference in sampling depth of the three beams provides the physical basis for the software logic and control algorithms to obtain elemental concentrations in a layered sample using FP analysis.

As discussed further below, x-ray tube 340 offers certain improvements in x-ray excitation energies providing yet further advantages.

Figure 4B:
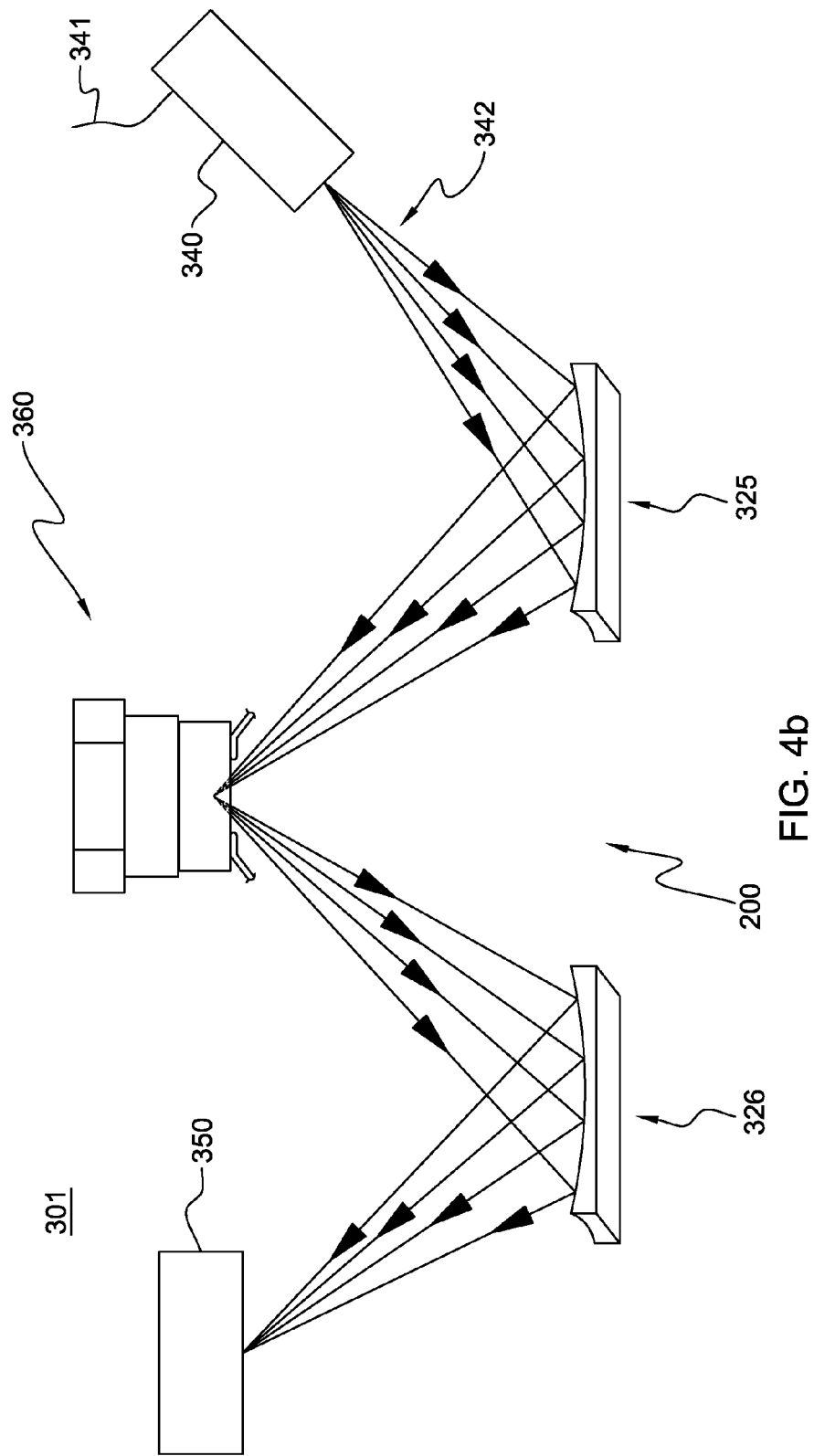

FIG. 4b depicts in schematic view an improved MWD XRF x-ray analysis engine 301, also improved in accordance with the present invention. The x-ray analysis engine may have a focal spot requiring alignment with the sample in an exemplary sample cell 360. Engine 301 also includes, in one embodiment, an x-ray source 340 (powered by supply 341) and detector 350. X-ray optics 325 and/or 326 can be placed in the excitation and/or detection paths of the engine. These optics provide a high degree of alignment with the sample spot to function at the requisite limits of detection discussed above.

Optics for either of these systems may include, for example, curved crystal monochromating optics such as those disclosed in commonly assigned U.S. Pat. Nos. 6,285,506; 6,317,483; 7,035,374; and 7,738,629; and/or multilayer optics; and/or HOPG optics; and/or x-ray filters; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506 and 7,209,545 are also useable. Each of the above-noted patents and patent applications is hereby incorporated herein by reference in its entirety.

Improved X-Ray Tube Targets:

The present invention is directed, in one embodiment, to the following improvements in x-ray source target materials and operating principles. Improved source target materials and operating kV potentials can offer further customization of the excitation energies, especially when used in combination with the optics described elsewhere herein. The words "tube" and/or "source" are used broadly herein to connote any type of device which produces x-rays from a target upon stimulation with, e.g., electron bombardment; and can include any end-window or side-window embodiments. The material layers below are applicable to both reflective surface and transmissive surface-style x-ray sources, without limitation.

Briefly summarizing, an x-ray tube may include a target on which electrons impinge to form a diverging x-ray beam. The target has a surface formed from first and second target materials, each target material tailored to emit a respective energy profile upon impingement by the electrons. A first x-ray optic may be provided for receiving the diverging x-ray beam and directing the beam toward the sample spot, the first x-ray optic monochromating the diverging x-ray beam to a first energy from the energy emitted by the first target material; and a second x-ray optic may also be provided, for receiving the diverging x-ray beam and directing the beam toward the sample spot, the second x-ray optic monochromating the diverging x-ray beam to a second energy from the energy emitted by the second target material. Fluorescence from the sample spot induced by the first and second monochromated energies is used to measure the concentration of at least one element in the sample, or separately measure elements in a coating and underlying substrate.

Three or more target materials may be used for the target. The target materials may be formed in separate layers on the target, or alloyed into a single layer, or a combination of both. The materials may emit characteristic energies and/or bremsstrallung; and the x-ray optics can be tailored to monochromate to particular x-ray energies. Sequencing between tube energies and/or optics can also be provided depending on the measurements needed.

Figure 5:
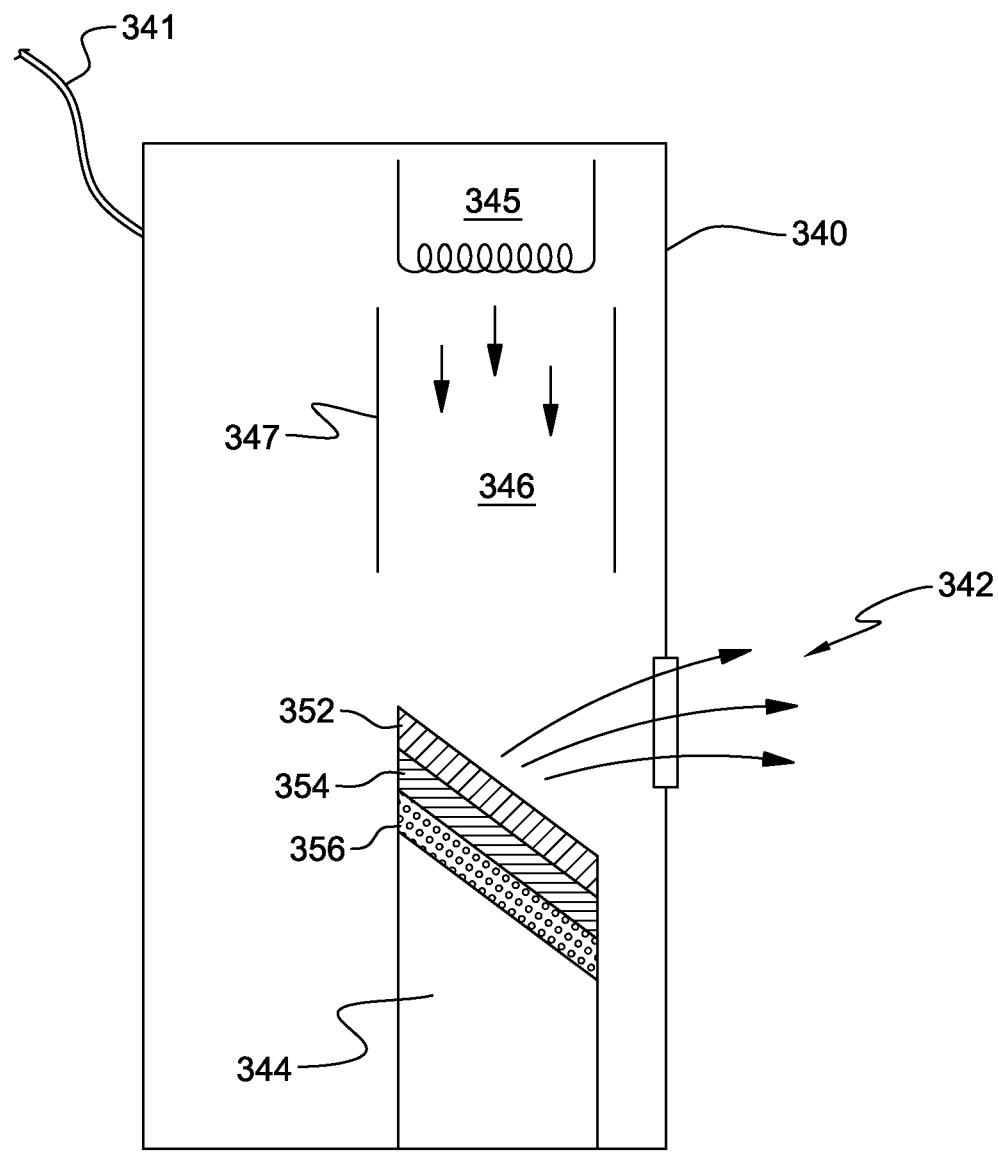
FIG. 5 is a schematic view of an exemplary x-ray tube having an anode surface formed from multiple materials in different layers, in accordance with the present invention.

In accordance with these aspects of the present invention, shown in FIG. 5 in schematic form is an exemplary compact, electron-bombardment x-ray tube 340 having an electron gun/filament 345 which may be heated (by applying a voltage) to a temperature such that electrons 346 are thermally emitted toward a target 344. These emitted electrons may be accelerated by an electric potential difference to target (e.g., anode) 344, which is covered with target materials, where they strike within a given surface area of the target. Divergent x-rays 342 are emitted from the target as a result of the collision between the accelerated electrons and the atoms of the target. To control the spot size, electromagnetic focusing 347 may be positioned between filament 345 and target (e.g., anode) 344.

In accordance with the present invention, target 344 may be coated with two or more materials which each provide different x-ray characteristic energies or other energy profiles in response to electrons 346. As one example shown in FIG. 5, three layers of three different materials 352, 354, and 356 respectively are formed on the upper surface of the target 344. Each of these materials may be chosen to have a different characteristic x-ray energy or other energy profile, such that the x-rays 342 emitted from the tube can contain different characteristic energies. In one example, an Fe upper layer (having a Kα line of approximately 6.4 keV) can be applied over a layer of Mo (having a Kα line of approximately 17.4 keV). This will enable more and predictable x-ray energies to be transmitted to the sample (possibly monochromated by the excitation optics discussed above for greater spectral narrowing). In another example, a Co upper layer (having a Kα line of approximately 6.9 keV) can be applied over a layer of Mo (having a Kα line of approximately 17.4 keV).

Though not required, in general the material with a lower x-ray characteristic energies should be placed on the upper layers, because higher kV electron beams will tend to penetrate the upper layers toward the lower layers, and more efficiently excite the lower layers to the exclusion of the upper layers; while lower kV electron beams will not penetrate the upper layers and therefore more efficiently excite the upper layer material at its characteristic energy.

The applied tube potential kV can also be controlled externally (e.g., through power cable 341) to separately produce certain desired characteristic energies (e.g., using a controllable power supply—not shown) to further optimize excitation of the desired x-ray energies by the multiple target material layers; in one embodiment using controllable sequencing techniques to alternatively employ different energies in sequence, depending on measurement requirements. Optic sequencing can be used separately or in combination with tube kV sequencing, including the use of shutters discussed above, physically shifting optics in as needed, or using the input aperture of the optic to "point" at separate areas of the target, which can be formed to have different materials across different surface areas, in one embodiment.

Figure 6:
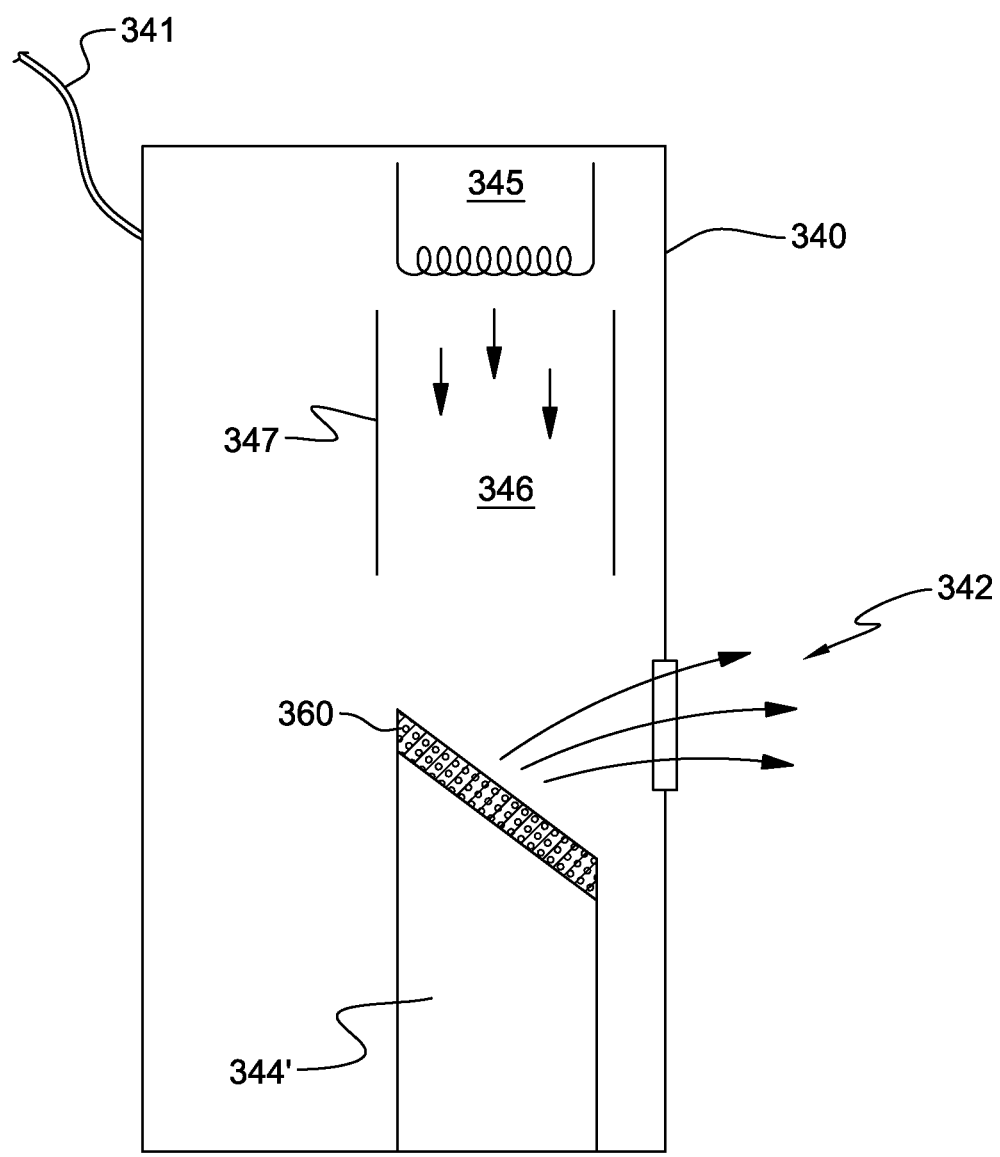
FIG. 6 is a schematic view of an exemplary x-ray tube having an anode surface formed from multiple materials in a single alloy layer, in accordance with the present invention.

In accordance with another aspect of the present invention, shown in FIG. 6 (where like numerals are used to connote like elements) in schematic form is a similar exemplary compact, electron-bombardment x-ray source 340 having an electron gun/filament 345 which may be heated (by applying a voltage) to a temperature such that electrons 346 are thermally emitted toward a target 344. These emitted electrons may be accelerated by an electric potential difference to target (e.g., anode) 344, which is covered with a target material, where they strike within a given surface area of the target. Divergent x-rays 342 are emitted from the target as a result of the collision between the accelerated electrons and the atoms of the target. To control the spot size, electromagnetic focusing 347 may be positioned between filament 345 and target (e.g., anode) 344.

In accordance with the present invention, target 344' may be coated with 2 or more materials which provide different x-ray characteristic energies or other energy profiles in response to electrons 346. As one example shown in FIG. 6, a single layer 360 of two different materials can be formed on the upper surface of the target 344'. As in FIG. 5, each of these materials may be chosen to have a different characteristic x-ray energy or other energy profile, such that the x-rays 342 emitted from the tube can contain different characteristic energies. In this example, however, the two different materials are alloyed into a common layer 360.

In one example, a Ce material (having a Kα line of approximately 34.7 keV) can be alloyed into a material of Mo (having a Kα line of approximately 17.4 keV). This will enable more and predictable x-ray energies to be transmitted to the sample from a single target layer (possibly monochromated by the excitation optics discussed above for greater spectral narrowing).

A combination of discrete material layers (FIG. 5) and alloyed material layers (FIG. 6) can also be used. For example, a Co upper layer (having a Kα line of approximately 6.9 keV) can be applied over the alloyed layer of Ce material (having a Kα line of approximately 34.7 keV) and Mo (having a Kα line of approximately 17.4 keV); together over a base, discrete layer of Mo only (having a Kα line of approximately 17.4 keV). In this example, the material with a lower x-ray characteristic energy (Co) is placed on the upper layers, because higher kV electron beams will tend to penetrate the upper layers toward the lower Ce/MO and Mo layers, and more efficiently excite the lower layers to the exclusion of the upper layers; while lower kV electron beams will not penetrate the upper layers and therefore more efficiently excite the upper layer material (Co) at its characteristic energy.

As above, the applied tube potential kV can be controlled to separately (e.g., through power cable 341) produce certain desired characteristic energies (e.g., using a controllable power supply—not shown) to further optimize excitation of the desired x-ray energies by the multiple target material layers; in one embodiment using controllable sequencing techniques to alternatively employ different energies in sequence, depending on measurement requirements. Optic sequencing can be used separately or in combination with tube kV sequencing, including the use of shutters discussed above, physically shifting optics in as needed, or using the input aperture of the optic to "point" at separate areas of the target, which can be formed to have different materials across different surface areas, in one embodiment.

The target materials and tube kV may be chosen to excite broader band Bremsstrallung energy from the source, which can then be spectrally narrowed (or not) by the monochromating optics, depending on system requirements. Any materials with predictable x-ray energy profiles may be used, including those mentioned above and others, including but not limited to Rh, W, Cr, etc. The target layers can be formed using various deposition and/or sputtering techniques.

Improved X-Ray Optics:

The present invention is also directed, in one embodiment, to the following improvements in x-ray optics, which can be used in combination with any of the improvements disclosed herein, including but not limited to the tube improvements above. Improved optics are disclosed for different elemental excitation ranges; for example, for different energies, different input focal distances (which are often, but not always, equivalent to the output focal distances), and different optic crystals. As used herein (but without limitation), low energy means about 3 to 7 keV; medium energy means about 15 to 20 keV; and high energy means about 30 to 40 keV or more.

Two optics are disclosed using different crystal materials: silicon (Si) and lithium-fluoride (LiF). The targeted energy selected by the optic needs to be the strong characteristic line from the anode target material in order to maximize the performance of the optic. LiF(200) can increase the monochromatic beam flux for a curved crystal optic. LiF has a wide rocking curve and can capture more photons from a larger source spot size, therefore, the diffraction efficiency from a larger source spot size is higher than that of an Si crystal. Thus, the diffraction flux is much larger than the Si crystal for a larger source spot size (e.g., >500 μm). In addition, LiF will bend more readily than Si for the same thickness. Both optics made of Si and LiF may have a Johann geometry design, as discussed elsewhere herein.

To achieve a high-intensity beam, geometries with very high collection solid angle are disclosed. A fully revolved ellipsoid point-to-point focusing of LiF is disclosed for this high-energy optic as shown in FIG. 4a. To achieve the full 360° ellipsoid optic, three similar ellipsoidal segments, each with about 120° rotational angles, are disclosed. The three segments are aligned to the same focal point and form a fully rotated optic. The total collection solid angle of this design can be >0.03 sr., which is about 40× larger than previous designs. Because the slight change of the incident angles for a point source emitting from the focus of the ellipse, the reflection energy bandwidth is broadened.

The spot sizes attainable with any of the above-described focusing optics can range from approximately 0.4 mm to 0.8 mm to 1.0 mm to 2.0 mm in diameter, facilitating analysis of small features on consumer products. In addition, the optics may produce spot sizes in any shape, depending on the shape of the optic.

Any of the layered optics discussed above can be implemented according to the techniques described in the commonly assigned, previously-filed U.S. patent application entitled X-RAY FOCUSING OPTIC HAVING MULTIPLE LAYERS WITH RESPECTIVE CRYSTAL ORIENTATIONS, filed Nov. 16, 2007 as Ser. No. 11/941,377, the entirety of which is incorporated by reference.

Figure 7:
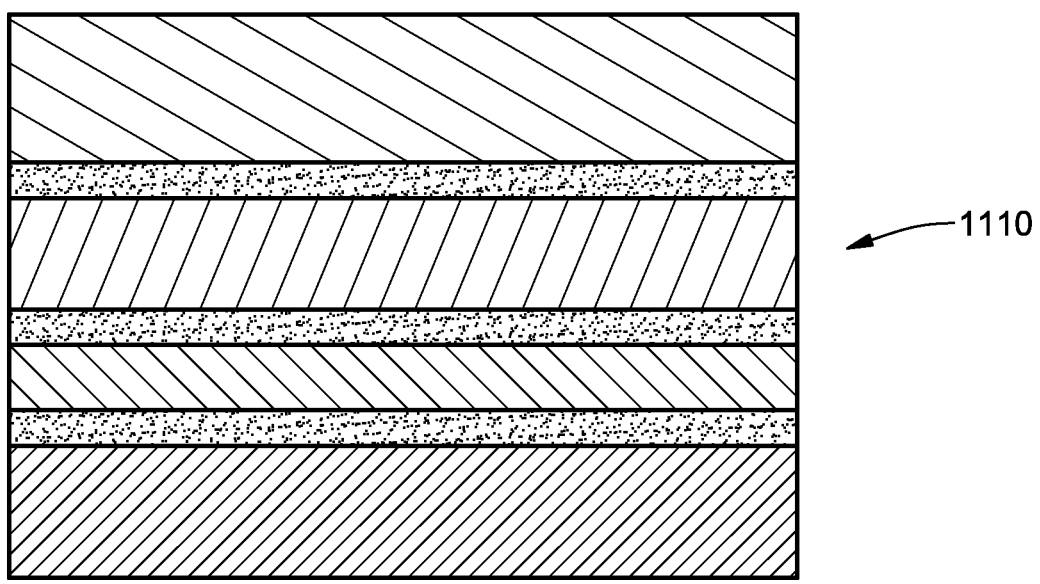
FIG. 7 depicts a finished, 4-layer x-ray optic structure, in accordance with an aspect of the present invention.

FIG. 7 shows one such resulting thin, layered structure 1110 having four finished layers, each with its own, predetermined crystalline orientation. Though four layers are shown in this example, the present invention can encompass any plurality of layers, depending on design parameters. And, not all the orientations need to be different. By predetermining the crystalline orientation of each layer, the diffraction properties of the structure as a whole can be optimized.

Each individual crystalline layer provides an individual diffractive effect. These diffractive effects can be separately modeled, and their collective effect in the final optic can then be predicted and implemented according to final design criteria. This stands in contrast to known "multi-layer" optics, having many layers of angstrom/nanometer thicknesses, each without an individual diffractive effect, but wherein the interactions between the layers result in an overall diffractive effect.

In another aspect of the present invention, layers of differing material composition can be employed in the same optic, with either the same or differing crystalline orientations between the layers (or mixes thereof); and layers of similar (or the same) material composition can be employed, again with either the same or differing crystalline orientations between the layers (or mixes thereof). In any of these aspects of the present invention, material-on-insulator may be used, or adhesive (e.g., epoxy) layers can be used to bind adjacent crystalline layers in accordance with the sequence of steps discussed in this incorporated Application.

Figure 8A:
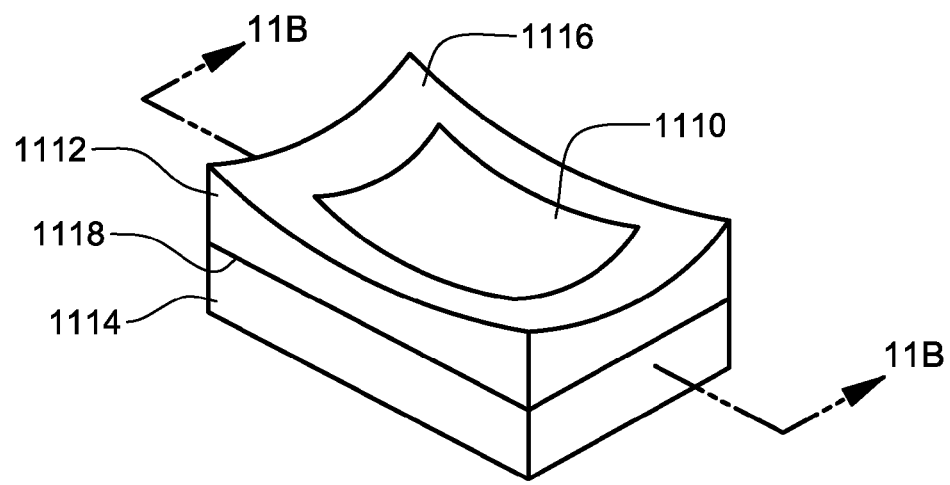
FIG. 8a depicts one embodiment of a point-focusing, doubly curved monochromating optic using the above-described layered structure.
Figure 8B:
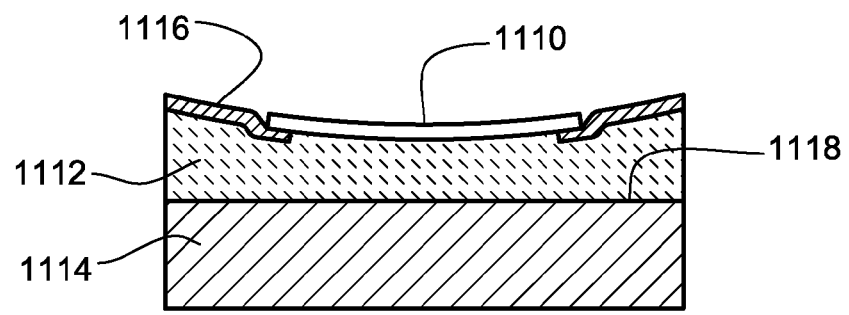
FIG. 8b is a cross-sectional, elevational view of the optic of FIG. 8a, taken along line A-A.

Structure 1110 can then be formed into a curved, monochromating optic, including a doubly-curved crystal (DCC) optic (or individual segments thereof). One embodiment of such a doubly-curved optical device is depicted in FIGS. 8a and 8b, and is described in detail in U.S. Pat. No. 6,285,506 B1, issued Sep. 4, 2001, the entirety of which is hereby incorporated herein by reference.

In the embodiment of FIG. 8a, a doubly-curved optical device includes the flexible layered optic 1110, a thick epoxy layer 1112 and a backing plate 1114. The structure of the device is shown further in the cross-sectional elevational view in FIG. 8b.

In this device, the epoxy layer 1112 holds and constrains the flexible layer 1110 to a selected geometry having a curvature. Preferably, the thickness of the epoxy layer is greater than 20 μm and the thickness of the flexible layer is greater than 5 μm. Further, the thickness of the epoxy layer is typically thicker than the thickness of the flexible layer.

The flexible layer can be one of a large variety of materials, including those discussed herein. The epoxy layer 1112 can be a paste type with viscosity in the order of $10^3$ to $10^4$ poise and 30 to 60 minutes pot life. The backing plate 1114 can be a solid object that bonds well with the epoxy. The surface 1118 of the backing plate can be flat (FIG. 8*a*) or curved, and its exact shape and surface finish are not critical to the shape and surface finish of the flexible layer. In the device of FIGS. 8*a*-*b*, a specially prepared backing plate is not required.

Surrounding the flexible layer may be a thin sheet of protection material 1116, such as a thin plastic, which is used around the flexible layer edge (see FIG. 8*a*). The protection material protects the fabrication mold so that the mold is reusable, and would not be necessary for a mold that is the exact size or smaller than the flexible layer, or for a sacrificial mold.

Figure 9:
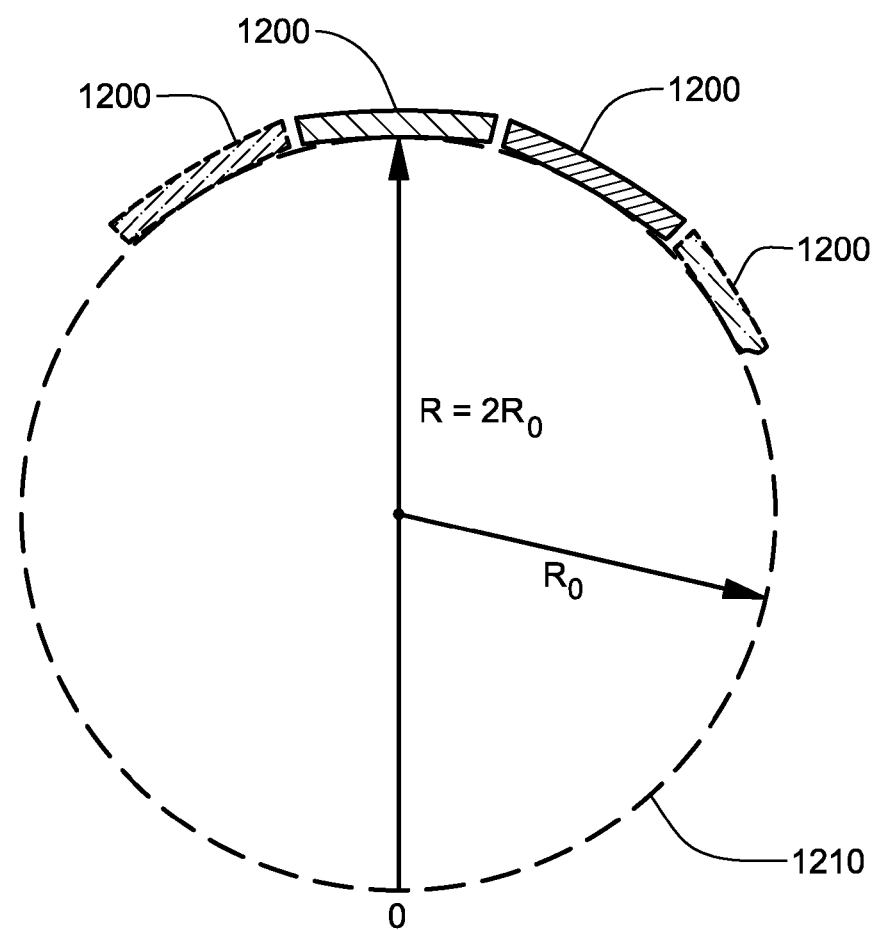
FIG. 9 depicts another possible embodiment of a focusing, curved monochromating optic (and illustrating Rowland circle geometry) using multiple instances (similar or different) of the above-described layered structure.

Any of the optics disclosed herein can be shaped in any way depending on the application, including but not limited to single directions of curvature (singly curved crystals—SCCs), double directions of curvature (doubly curved crystals—DCCs), and other designs. Doubly-curved optical devices, such as doubly-curved crystal (DCC) optics, may be used in material analysis to collect and focus x-rays from a large solid angle and increase the usable flux from an x-ray source. Three-dimensional focusing of characteristic x-rays can be achieved by diffraction from a toroidal crystal used with a small x-ray source. This point-to-point Johan geometry is illustrated in FIG. 9. The diffracting planes of each crystal optic element 1200 can be parallel to the crystal surface. If the focal circle 1210 containing a point source and the focal point has radius $R_0$, then the crystal surface has, for example, a radius R of curvature of $2R_0$ in the plane of the focal circle and a radius of curvature of $r=2R_0 \sin^2 \theta_{Brag}$ in the perpendicular plane, with the radius centered on a line segment drawn between the source and the focal point. X-rays diverging from the source, and incident on the crystal surface at angles within the rocking curve of the crystal will be reflected efficiently to the focal or image point. The monochromatic flux density at the focal point for a DCC-based system is several orders of magnitude greater than that of conventional systems with higher power sources and similar source to object distances. This increase yields a very high sensitivity for use in many different applications, including (as described herein) x-ray fluorescence and diffraction.

As a further enhancement, FIG. 9 illustrates that the optical device may comprise multiple doubly-curved crystal optic elements 1200 arranged in a grid pattern about the Rowland circle, each element formed from a flexible structure 1110 as discussed above (either with similar or different element-to-element layer structures). Such a structure may be arranged to optimize the capture and redirection of divergent radiation via Bragg diffraction. In one aspect, a plurality of optic crystals having varying atomic diffraction plane orientations can be used to capture and focus divergent x-rays towards a focal point. In another aspect, a two or three dimensional matrix of crystals can be positioned relative to an x-ray source to capture and focus divergent x-rays in three dimensions. Further details of such a structure are presented in the above-incorporated U.S. Pat. No. 7,035,374 B1, issued Apr. 25, 2006.

The layered optic structures offer the following advantages:

The optic's mosaicity and rocking curves are controlled by layer orientation design.
The efficiency of the optic is increased—each layer (with its own custom orientation) can have its own field of view, resulting in a composite field of view which increases efficiency and allows the optic to accommodate a larger source spot size. And, by accommodating a larger source spot size, system implementation is easier.

The bandwidth (i.e., monochromatization) of the optic can be controlled, and, advantageously, increased in certain monochromating applications.

Figure 10:
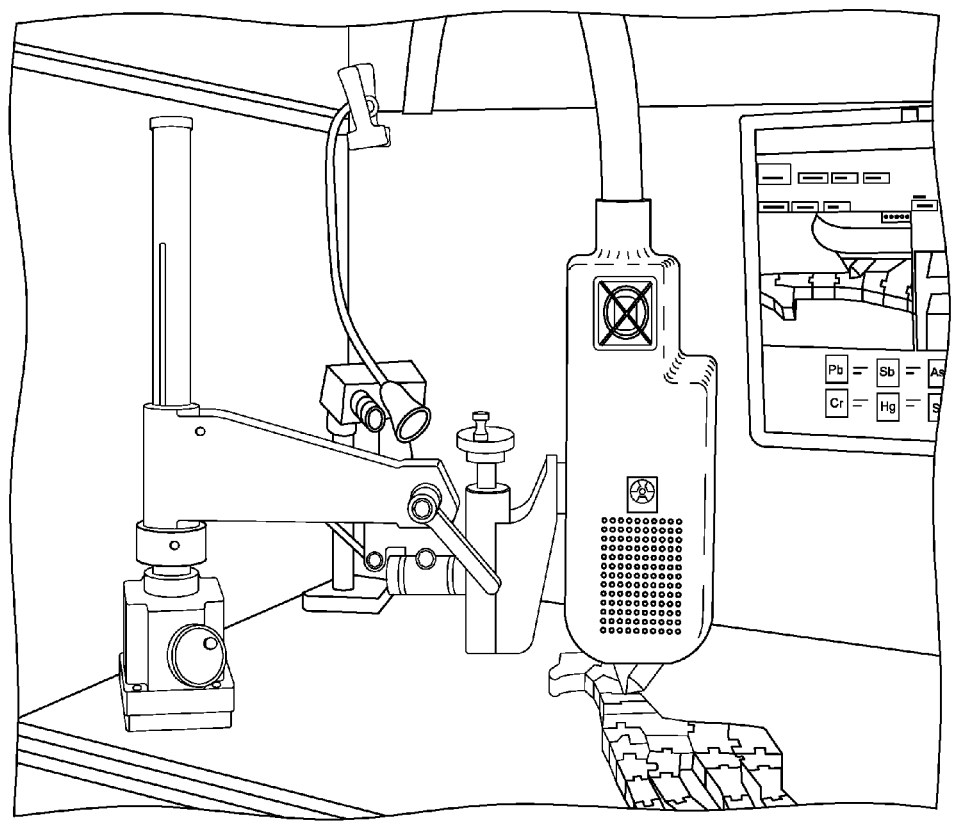
FIG. 10 is a perspective view of an analyzer engine suspended over a sample, in accordance with the principles of the present invention.

Improved Analyzer System:

An exemplary EDXRF analyzer system constructed in accordance with the present invention, using an exemplary SDD detector, an improved source, and low, medium, and high energy optics, is shown in FIG. 10, measuring a sample toy.

A fundamental parameter (FP) technique for monochromatic systems with Compton/Rayleigh (C/R) modeling may be used to process the x-ray fluorescence data detected from a sample stimulated with multiple, monochromatic beams generated by the optics and/or tubes discussed above. The FP technique is based on a single energy excitation beam and is suitable for bulk and homogenous measurements. Multiple monochromatic beams can be used, to sense different parts of the spectrum, and to de-convolute the toxins the painted layers and separately in the substrate.

A spectral processor (SP) may be used for fitting an energy dispersive X-ray fluorescence (EDXRF) spectrum based on multiple monochromatic beam excitation. The raw spectral data from the detector in a count vs. energy spectrum can be used for the input. A number of techniques can be utilized to account for various components in the spectrum such as a Gaussian modeling for peak fitting. Noise from the system and detector is also considered.

The fundamental parameters (FP) based technique is also useful for coating layer quantitative analysis. In this technique, the absorption, fluorescence, and scattering, are modeled based on a number of measured factors. Due to the use of monochromatic beams, the calculations can simplified, compared to the FP methods used for polychromatic excitation.

The layered-mode FP may require spectra from the combination of paint with the substrate, then from the substrate only, to resolve the separate compositions of a paint/substrate sample. One technical challenge is that the mass per unit area of the paint is unknown due to the low-Z elements (C, H, O) in the paint that cannot be detected. This mass per unit area for the coating, called ρt (density×thickness), should be determined in order to calculate the mass fraction of toxins. With two or more monochromatic beams, the toxin concentrations in the paint, and substrate separately, sample can be determined.

Figure 11:
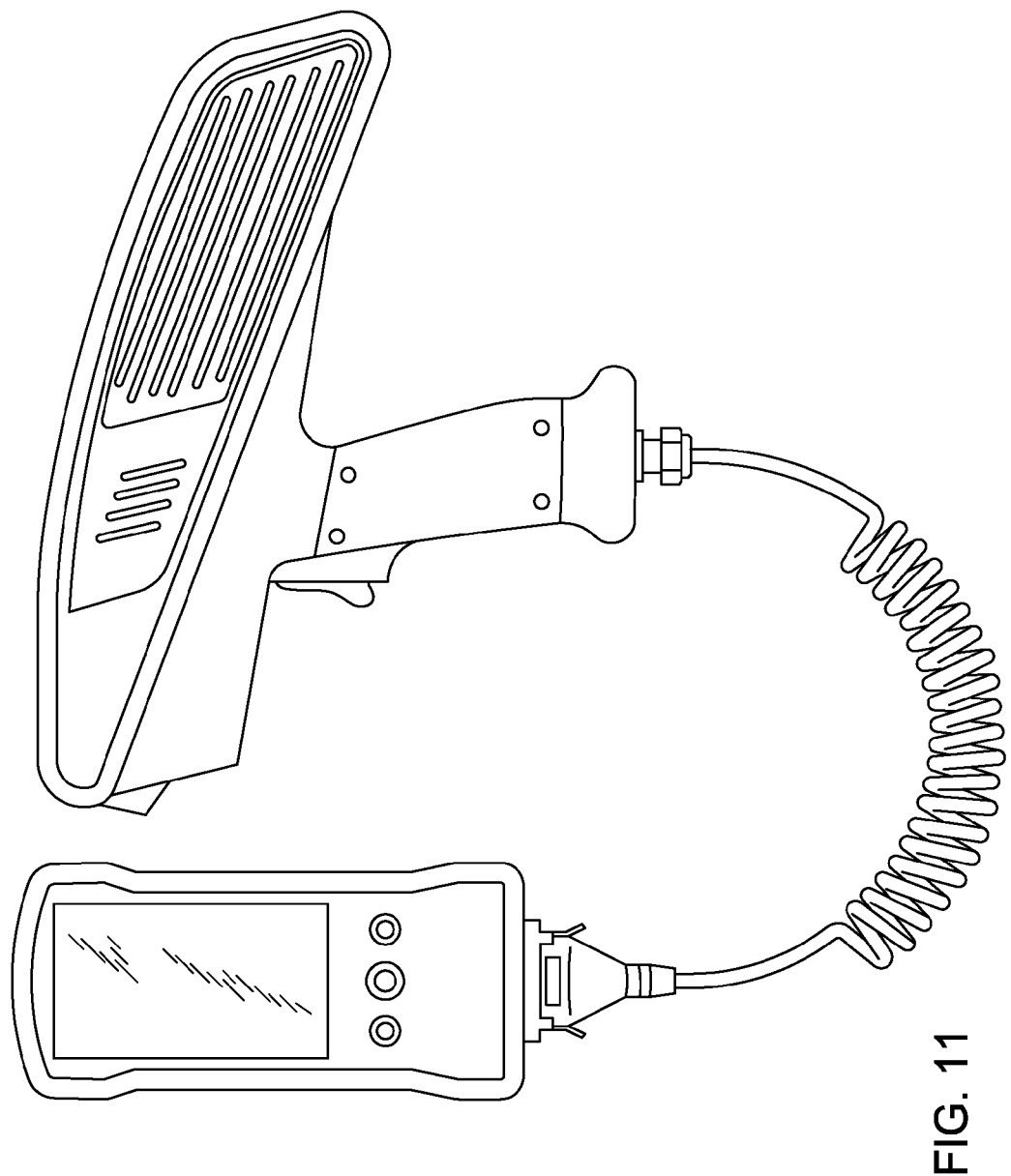
FIG. 11 is a perspective view of an exemplary handheld x-ray analysis instrument and related human interface module, in accordance with the principles of the present invention.

Also, in accordance with the present invention, and with reference to FIG. 11, a smaller, "handheld" x-ray analyzer can also be implemented according to the principles of the present invention. Handheld x-ray analyzers have gained in popularity over the last few years because of their transportability and ease of use. Also shown in FIG. 11 is a human interface module, which may include the user interface, FP processor, and/or a power source for the handheld analyzer. Such an interface may also be integral to the analyzer.

Figure 12:
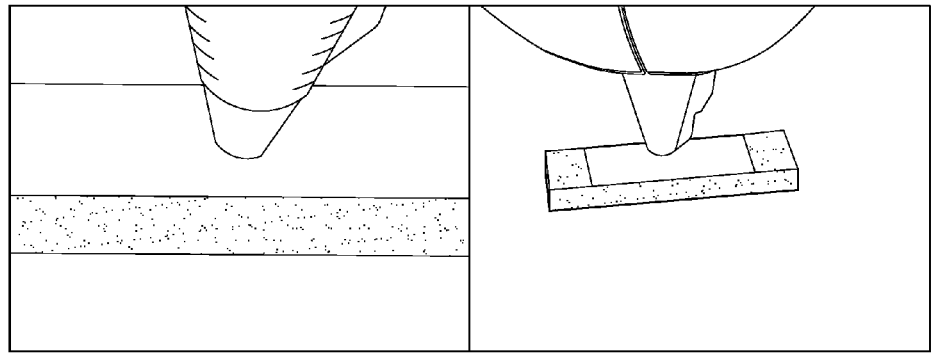
FIG. 12 is an exemplary graphical user interface of the analyzer of FIG. 10 and/or FIG. 11.
Figure 12:
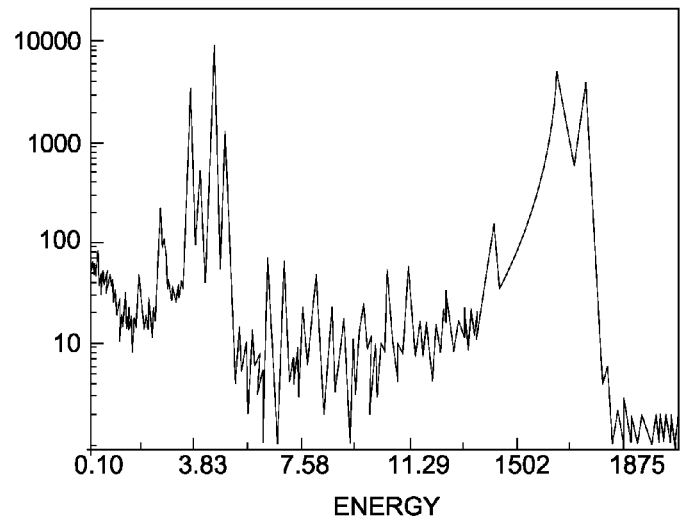

An example graphic user interface (GUI) for either of these systems is shown in FIG. 11. This exemplary GUI allows user selections of sample types, displays 10 element concentrations, and related spectra. The GUI may also display a live image of the sample to assist with sample positioning. A snap shot of the GUI is shown in FIG. 12.

The process steps depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray analysis apparatus for analyzing a sample spot, comprising:
    an x-ray tube comprising a target on which electrons impinge to form a diverging x-ray beam, the target having a surface formed from first and second target materials, each target material tailored to emit a respective energy profile upon impingement by the electrons;
    a first x-ray optic for receiving the diverging x-ray beam and directing the beam toward the sample spot, the first x-ray optic monochromating the beam to a first energy from the energy profile emitted by the first target material;
    a second x-ray optic for receiving the diverging x-ray beam and directing the beam toward the sample spot, the second x-ray optic monochromating the beam to a second energy from the energy profile emitted by the second target material; and
    a detector to receive fluorescence from the sample spot induced by the first and second monochromated energies and indicative of a concentration of at least one element in the sample.

2. The apparatus of claim 1, further comprising:
    the target of the x-ray tube having a surface formed from a third target material, the third target material tailored to emit a respective energy profile upon impingement by the electrons; and
    a third x-ray optic for receiving the diverging x-ray beam and directing the beam toward the sample spot, the third x-ray optic monochromating the beam to a third energy from the energy profile emitted by the third target material.

3. The apparatus of claim 2, wherein the first x-ray optic monochromates characteristic energy from the target and the second and/or third x-ray optic monochromates bremsstrahlung energy from the target.

4. The apparatus of claim 1, wherein the x-ray optics are curved diffracting optics, for receiving the diverging x-ray beam from the x-ray tube and focusing the beam at the sample spot.

5. The apparatus of claim 4, wherein the x-ray optics are focusing monochromating optics.

6. The apparatus of claim 5, wherein the x-ray optics are doubly-curved crystal optics, or HOPG optics, or multi-layer optics.

7. The apparatus of claim 1, wherein the first and/or second optic comprises a curved crystal diffracting optic comprising multiple layers, each layer having its own diffractive effect on the incident x-ray beam.

8. The apparatus of claim 7, wherein the layers of the first and/or second optic comprise LiF.

9. The apparatus of claim 8, wherein the first and/or second optic comprising LiF layers further comprises at least one segment bent into a curved shape.

10. The apparatus of claim 9, wherein the first and/or second optic comprising LiF layers further comprises multiple segments, each segment bent into a curved shape, and arranged into a curved pattern.

11. The apparatus of claim 6, wherein the curved pattern comprises a fully rotated, 360 degree pattern.

12. The apparatus of claim 1, wherein the first x-ray optic monochromates characteristic energy from the target and the second x-ray optic monochromates bremsstrahlung energy from the target.

13. The apparatus of claim 1, wherein fluorescence from the sample spot induced by the first and second monochromated energies is used to measure the concentration of at least one element separately in a coating and a substrate of the sample.

14. The apparatus of claim 1, wherein each target material of the first and second target materials is formed in a separate layer on the target.

15. The apparatus of claim 1, wherein each target material of the first and second target materials is combined into a single alloy layer on the target.

16. The apparatus of claim 1, wherein:
    one of the first and second target materials is formed in a first layer on the target; and
    at least two target materials are combined into a second, alloy layer on the target.

* * * * *